United States Patent
Basson et al.

(10) Patent No.: US 9,294,814 B2
(45) Date of Patent: *Mar. 22, 2016

(54) SIMULATION METHOD AND SYSTEM (71) Applicant: International Business Machines Corporation, Armonk, NY (US)

(72) Inventors: Sara H. Basson, White Plains, NY (US); Dimitri Kanevsky, Ossining, NY (US); Edward Emile Kelley, Wappingers Falls, NY (US); Bhuvana Ramabhadran, Mount Kisco, NY (US)

(73) Assignee: International Business Machines Corporation, Armonk, NY (US)

( * ) Notice: Subject to any disclaimer, the term of this patent is extended or adjusted under 35 U.S.C. 154(b) by 379 days.

This patent is subject to a terminal disclaimer.

(21) Appl. No.: 13/901,700

(22) Filed: May 24, 2013

(65) Prior Publication Data
US 2013/0254794 A1 Sep. 26, 2013

Related U.S. Application Data (63) Continuation of application No. 13/460,926, filed on May 1, 2012, now Pat. No. 8,493,410, which is a continuation of application No. 12/137,606, filed on Jun. 12, 2008, now Pat. No. 8,237,742.

(51) Int. Cl.
| | |
|---|---|
| G10L 21/00 | (2013.01) |
| G10L 21/06 | (2013.01) |
| H04N 21/442 | (2011.01) |
| G11B 27/028 | (2006.01) |
| G06F 19/00 | (2011.01) |
| G11B 27/034 | (2006.01) |
| G11B 27/28 | (2006.01) |
| G10L 21/013 | (2013.01) |

(52) U.S. Cl.
CPC ...... H04N 21/44213 (2013.01); G06F 19/3437 (2013.01); G10L 21/00 (2013.01); G10L 21/06 (2013.01); G11B 27/028 (2013.01); G11B 27/034 (2013.01); G11B 27/28 (2013.01); G10L 2021/0135 (2013.01); G10L 2021/065 (2013.01)

(58) Field of Classification Search
None
See application file for complete search history.

(56) References Cited

U.S. PATENT DOCUMENTS

| | | | |
|---|---|---|---|
| 4,739,401 | A | 4/1988 | Sacks et al. |
| 5,227,863 | A | 7/1993 | Bilbrey et al. |
| 5,802,281 | A | 9/1998 | Clapp et al. |

(Continued)

OTHER PUBLICATIONS

Final Office Action (Mail Date Jul. 23, 2013) for U.S. Appl. No. 13/484,320, filed May 31, 2012.
Amendment after Final filed Sep. 16, 2013 in response to Office Action (Mail Date Jul. 23, 2013) for U.S. Appl. No. 13/484,320, filed May 31, 2012.
Notice of Allowance (Mail Date Sep. 26, 2013) for U.S. Appl. No. 13/484,320, filed May 31, 2012.

(Continued)

*Primary Examiner* — Joni Richer
(74) *Attorney, Agent, or Firm* — Schmeiser, Olsen & Watts; John Pivnichny

(57) ABSTRACT

A simulation method and system. A computing system receives a first audio and/or video data stream. The first audio and/or video data stream includes data associated with a first person. The computing system monitors the first audio and/or video data stream. The computing system identifies emotional attributes comprised by the first audio and/or video data stream. The computing system generates a second audio and/or video data stream associated with the first audio and/or video data stream. The second audio and/or video data stream includes the data without the emotional attributes. The computing system stores the second audio and/or video data stream.

16 Claims, 8 Drawing Sheets

(56) References Cited

U.S. PATENT DOCUMENTS

| | | |
|---|---|---|
| 6,006,241 A | 12/1999 | Purnaveja et al. |
| 6,931,147 B2 | 8/2005 | Colmenarez et al. |
| 7,035,807 B1 | 4/2006 | Brittain et al. |
| 7,085,719 B1 | 8/2006 | Shambaugh et al. |
| 7,283,962 B2 | 10/2007 | Meyerhoff et al. |
| 7,607,097 B2 | 10/2009 | Janakiraman et al. |
| 7,627,475 B2 | 12/2009 | Petrushin |
| 8,036,899 B2 | 10/2011 | Sobol-Shikler |
| 8,126,220 B2 | 2/2012 | Greig |
| 8,237,742 B2 | 8/2012 | Basson et al. |
| 8,259,992 B2 | 9/2012 | Basson et al. |
| 8,392,195 B2 | 3/2013 | Basson et al. |
| 8,493,410 B2 | 7/2013 | Basson et al. |
| 8,644,550 B2 | 2/2014 | Basson et al. |
| 2003/0108241 A1 | 6/2003 | Colmenarez et al. |
| 2004/0197750 A1 | 10/2004 | Donaher et al. |
| 2005/0159958 A1 | 7/2005 | Yoshimura |
| 2006/0122834 A1 | 6/2006 | Bennett et al. |
| 2007/0061352 A1 | 3/2007 | Dimatrova et al. |
| 2007/0124360 A1 | 5/2007 | Ittycheriah et al. |
| 2007/0192108 A1 | 8/2007 | Konchitsky |
| 2007/0230439 A1 | 10/2007 | Milstein et al. |
| 2007/0277092 A1 | 11/2007 | Basson et al. |
| 2007/0299888 A1 | 12/2007 | Thornton et al. |
| 2008/0177536 A1 | 7/2008 | Sherwani et al. |
| 2008/0268408 A1 | 10/2008 | Zernzach |
| 2008/0273765 A1 | 11/2008 | Tsumimura |
| 2008/0275830 A1 | 11/2008 | Greig et al. |
| 2009/0297029 A1 | 12/2009 | Cazier |
| 2009/0299748 A1 | 12/2009 | Basson et al. |
| 2009/0310939 A1 | 12/2009 | Basson et al. |
| 2009/0313015 A1 | 12/2009 | Basson et al. |
| 2009/0319265 A1 | 12/2009 | Wittenstein et al. |
| 2010/0191037 A1 | 7/2010 | Cohen et al. |
| 2010/0299131 A1 | 11/2010 | Lanham et al. |
| 2012/0213489 A1 | 8/2012 | Basson et al. |
| 2012/0239393 A1 | 9/2012 | Basson et al. |
| 2012/0246669 A1 | 9/2012 | Basson et al. |

OTHER PUBLICATIONS

Office Action (Mail Date Mar. 14, 2013) for U.S. Appl. No. 13/484,320, filed May 31, 2012.

Amendment filed May 20, 2013 in response to Office Action (Mail Date Mar. 14, 2013) for U.S. Appl. No. 13/484,320, filed May 31, 2012.

Chen et al.; Multimodal Human Emotion/Expression Recognition; Third IEEE International Conference on Automatic Face and Gesture Recognition; Apr. 14-17, 1998; pp. 366-371.

Pivik et al.; Using Virtual Reality to Teach Disability Awareness; J. Educational Computing Research, vol. 26(2) 2002 Baywood Publishing Co Inc.; pp. 203-218, May 2002.

Office Action (Mail Date Jun. 30, 2011) for U.S. Appl. No. 12/137,606, filed Jun. 13, 2008.

Amendment filed Sep. 20, 2011 in response to Office Action (Mail Date Jun. 30, 2011) for U.S. Appl. No. 12/137,606, filed Jun. 13, 2008.

Office Action (Mail Date Jan. 12, 2012) for U.S. Appl. No. 12/137,606, filed Jun. 13, 2008.

Amendment filed Mar. 16, 2012 in response to Office Action (Mail Date Jan. 12, 2012) for U.S. Appl. No. 12/137,606, filed Jun. 13, 2008.

Notice of Allowance (Mail Date Mar. 29, 2012) for U.S. Appl. No. 12/137,606, filed Jun. 13, 2008.

Office Action (Mail Date Jan. 12, 2012) for U.S. Appl. No. 12/138,966, filed Jun. 13, 2008.

Amendment filed Mar. 26, 2012 in response to Office Action (Mail Date Jan. 12, 2012) for U.S. Appl. No. 12/138,966, filed Jun. 13, 2008.

Notice of Allowance (Mail Date Oct. 26, 2012) for U.S. Appl. No. 13/484,323, filed May 31, 2012.

Notice of Allowance (Mail Date Apr. 25, 2012) for U.S. Appl. No. 12/138,996, filed Jun. 31, 2008.

Office Action (Mail Date Nov. 7, 2012) for U.S. Appl. No. 13/460,926, filed May 1, 2012.

Amendment filed Dec. 19, 2012 in response to Office Action (Mail Date Nov. 7, 2012) for U.S. Appl. No. 13/460,926, filed May 1, 2012.

Notice of Allowance (Mail Date Apr. 3, 2013) for U.S. Appl. No. 13/460,926, filed May 1, 2012.

SIMULATION METHOD AND SYSTEM

This application is a continuation application claiming priority to Ser. No. 13/460,926, filed May 1, 2012, now U.S. Pat. No. 8,493,410, issued Jul. 23, 2013, which is a continuation application claiming priority to Ser. No. 12/137,606, filed Jun. 12, 2008, now U.S. Pat. No. 8,237,742, issued Aug. 7, 2012.

FIELD

The present invention relates to a method and associated system for simulating emotional attributes within audio/video data streams.

BACKGROUND

Modifying multiple data files typically comprises an inefficient process with little flexibility. Accordingly, there exists a need in the art to overcome the deficiencies and limitations described herein.

SUMMARY

The present invention provides a simulation method, comprising: receiving, by a computing system, a first audio/video data stream, wherein said first audio/video data stream comprises first speech data associated with a first person; monitoring, by said computing system, said first audio/video data stream; identifying, by said computing system in response to said monitoring said first audio/video data stream, first emotional attributes comprised by said first audio/video data stream; generating, by said computing system in response to said identifying said first emotional attributes, an audio data stream associated with said first audio/video data stream, wherein said audio data stream comprises said first speech data, and wherein said audio data stream does not comprise said first emotional attributes; storing, by said computing system, said audio data stream; identifying, by said computing system, a first attribute of said first emotional attributes; associating, by said computing system, a first audible portion of said audio data stream with said first attribute; generating, by said computing system, an audible label for said first audible portion of said audio data stream, wherein said audible label indicates said first attribute; applying, by said computing system, said audible label to said first audible portion of said audio data stream; generating, by said computing system in response to said applying, a second audio data stream associated with said audio data stream, wherein said second audio data stream comprises said audio data stream and said first audible portion of said audio data stream comprising said audible label; generating, by said computing system, a video data stream associated with said audio/video data stream, wherein said video data stream comprises video data associated with said first person, and wherein said video data does not comprise said first emotional attributes; associating, by said computing system, a first visual object of said video data with said first attribute of said first emotional attributes; generating, by said computing system, a viewable label for said first visual object, wherein said viewable label indicates said first attribute of said first emotional attributes; applying, by said computing system, said viewable label to said first visual object; generating, by said computing system in response to said applying, a second audio/video data stream associated with said second video data stream and said second audio data stream, wherein said second audio/video data stream comprises said audio data stream, said first audible portion of said audio data stream comprising said audible label, said second video data, and said first visual object comprising said viewable label; and storing, by said computing system, said second audio/video data stream.

The present invention provides a computer program product, comprising a computer storage device storing a computer readable program code, said computer readable program code configured to perform a method upon being executed by a processor of a computing system, said method comprising: receiving, by said computing system, a first audio/video data stream, wherein said first audio/video data stream comprises first speech data associated with a first person; monitoring, by said computing system, said first audio/video data stream; identifying, by said computing system in response to said monitoring said first audio/video data stream, first emotional attributes comprised by said first audio/video data stream; generating, by said computing system in response to said identifying said first emotional attributes, an audio data stream associated with said first audio/video data stream, wherein said audio data stream comprises said first speech data, and wherein said audio data stream does not comprise said first emotional attributes; storing, by said computing system, said audio data stream; identifying, by said computing system, a first attribute of said first emotional attributes; associating, by said computing system, a first audible portion of said audio data stream with said first attribute; generating, by said computing system, an audible label for said first audible portion of said audio data stream, wherein said audible label indicates said first attribute; applying, by said computing system, said audible label to said first audible portion of said audio data stream; generating, by said computing system in response to said applying, a second audio data stream associated with said audio data stream, wherein said second audio data stream comprises said audio data stream and said first audible portion of said audio data stream comprising said audible label; generating, by said computing system, a video data stream associated with said audio/video data stream, wherein said video data stream comprises video data associated with said first person, and wherein said video data does not comprise said first emotional attributes; associating, by said computing system, a first visual object of said video data with said first attribute of said first emotional attributes; generating, by said computing system, a viewable label for said first visual object, wherein said viewable label indicates said first attribute of said first emotional attributes; applying, by said computing system, said viewable label to said first visual object; generating, by said computing system in response to said applying, a second audio/video data stream associated with said second video data stream and said second audio data stream, wherein said second audio/video data stream comprises said audio data stream, said first audible portion of said audio data stream comprising said audible label, said second video data, and said first visual object comprising said viewable label; and storing, by said computing system, said second audio/video data stream.

The present invention provides a computing system comprising a processor coupled to a computer-readable memory unit, said memory unit comprising a computer readable code configured to be executed by the processor to perform a method comprising: receiving, by said computing system, a first audio/video data stream, wherein said first audio/video data stream comprises first speech data associated with a first person; monitoring, by said computing system, said first audio/video data stream; identifying, by said computing system in response to said monitoring said first audio/video data stream, first emotional attributes comprised by said first audio/video data stream; generating, by said computing system in response to said identifying said first emotional attributes, an audio data stream associated with said first audio/video data stream, wherein said audio data stream comprises said first speech data, and wherein said audio data stream does not comprise said first emotional attributes; storing, by said computing system, said audio data stream; identifying, by said computing system, a first attribute of said first emotional attributes; associating, by said computing system, a first audible portion of said audio data stream with said first attribute; generating, by said computing system, an audible label for said first audible portion of said audio data stream, wherein said audible label indicates said first attribute; applying, by said computing system, said audible label to said first audible portion of said audio data stream; generating, by said computing system in response to said applying, a second audio data stream associated with said audio data stream, wherein said second audio data stream comprises said audio data stream and said first audible portion of said audio data stream comprising said audible label; generating, by said computing system, a video data stream associated with said audio/video data stream, wherein said video data stream comprises video data associated with said first person, and wherein said video data does not comprise said first emotional attributes; associating, by said computing system, a first visual object of said video data with said first attribute of said first emotional attributes; generating, by said computing system, a viewable label for said first visual object, wherein said viewable label indicates said first attribute of said first emotional attributes; applying, by said computing system, said viewable label to said first visual object; generating, by said computing system in response to said applying, a second audio/video data stream associated with said second video data stream and said second audio data stream, wherein said second audio/video data stream comprises said audio data stream, said first audible portion of said audio data stream comprising said audible label, said second video data, and said first visual object comprising said viewable label; and storing, by said computing system, said second audio/video data stream.

The present invention provides a process for supporting computer infrastructure, said process comprising providing at least one support service for at least one of creating, integrating, hosting, maintaining, and deploying computer-readable code in a computing system, wherein the code in combination with the computing system is capable of performing a method comprising: receiving, by said computing system, a first audio/video data stream, wherein said first audio/video data stream comprises first speech data associated with a first person; monitoring, by said computing system, said first audio/video data stream; identifying, by said computing system in response to said monitoring said first audio/video data stream, first emotional attributes comprised by said first audio/video data stream; generating, by said computing system in response to said identifying said first emotional attributes, an audio data stream associated with said first audio/video data stream, wherein said audio data stream comprises said first speech data, and wherein said audio data stream does not comprise said first emotional attributes; storing, by said computing system, said audio data stream; identifying, by said computing system, a first attribute of said first emotional attributes; associating, by said computing system, a first audible portion of said audio data stream with said first attribute; generating, by said computing system, an audible label for said first audible portion of said audio data stream, wherein said audible label indicates said first attribute; applying, by said computing system, said audible label to said first audible portion of said audio data stream; generating, by said computing system in response to said applying, a second audio data stream associated with said audio data stream, wherein said second audio data stream comprises said audio data stream and said first audible portion of said audio data stream comprising said audible label; generating, by said computing system, a video data stream associated with said audio/video data stream, wherein said video data stream comprises video data associated with said first person, and wherein said video data does not comprise said first emotional attributes; associating, by said computing system, a first visual object of said video data with said first attribute of said first emotional attributes; generating, by said computing system, a viewable label for said first visual object, wherein said viewable label indicates said first attribute of said first emotional attributes; applying, by said computing system, said viewable label to said first visual object; generating, by said computing system in response to said applying, a second audio/video data stream associated with said second video data stream and said second audio data stream, wherein said second audio/video data stream comprises said audio data stream, said first audible portion of said audio data stream comprising said audible label, said second video data, and said first visual object comprising said viewable label; and storing, by said computing system, said second audio/video data stream.

The present invention advantageously provides a system and associated method capable of modifying multiple data files.

BRIEF DESCRIPTION

DETAILED DESCRIPTION

Figure 1:
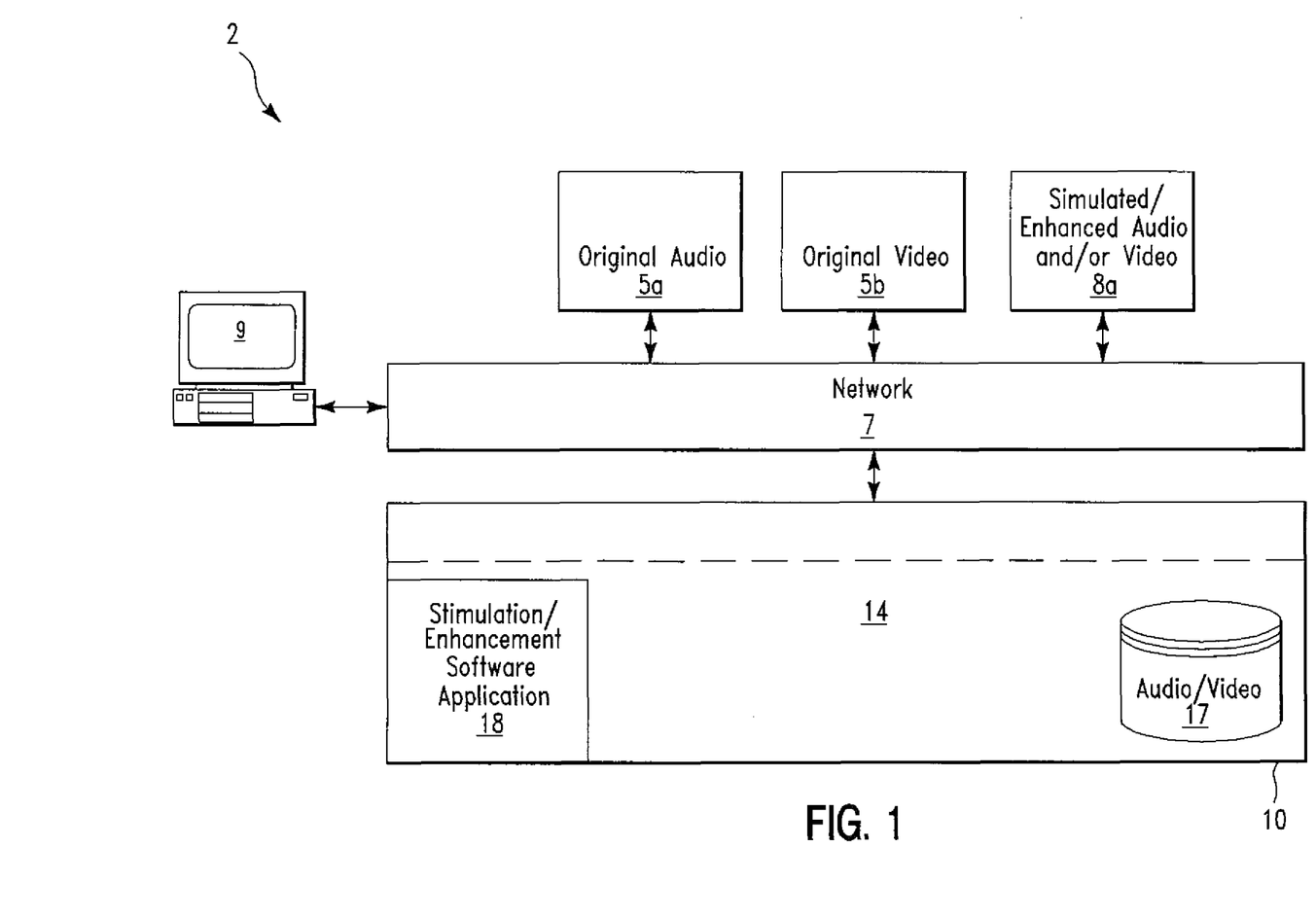
FIG. 1 illustrates a block diagram view of a system for simulating disabilities and/or enhancing audio/video data streams, in accordance with embodiments of the present invention.

FIG. 1 illustrates a block diagram view of a system 2 for simulating disabilities and/or enhancing audio/video data streams, in accordance with embodiments of the present invention. System 2 performs a process for:

1. Simulating an environment that a disabled person (e.g., an autistic person) perceives. The simulated environment is used by a person without a disability (e.g., product designers, parents, teachers, managers, etc) in order to increase awareness and sensitivities to people having disabilities. System 2 monitors and modifies inputted audio/video media (e.g., an audio/video data stream associated with, inter alia, a television show, a movie, a live event (e.g., a concert, a live speaker, etc.), etc. Audio and video media are independently modified to remove emotion cues and focus on given objects. System 2 monitors real-time events (e.g., movies, television shows, concerts, etc) and presents them in a modified manner on a visual display or in a virtual simulator. Real world audio and video media is obtained from external sensors such as microphones, cameras, and biometric sensors. Audio and video media from virtual simulators is interpreted directly via source code. System 2 identifies (e.g., by detecting specific facial expressions, by detecting specific vocal expressions, etc) and removes emotional events (e.g., by removing and replacing video comprising specific facial expressions, by removing and replacing specific vocal expressions, etc) from audio and video media. As a first example, video data illustrating smiling faces may be modified or replaced to show neutral, expressionless faces. As a second example, audio data that comprises emotion (e.g., happy or sad voices, exited voices, etc) may be modified or replaced to sound monotone and expressionless. System 2 deconstructs real-time audio and video media and transforms it such that a viewer without a disability (e.g., a non-autistic person) may experience what a viewer with a disability (e.g., an autistic person) may perceive. The identification and removal of emotion from audio and video media may comprise a hybrid process that involves automatic and human editing. Alternatively, the identification and removal of emotion from audio and video media may comprise an automatic process. Additionally, system 2 may remove a focus on central objects (i.e., from video media). For example, an autistic person may have difficulty identifying a central or main object in a visual image and therefore system 2 may identifies the central object in the visual image and modifies the visual image such that it no longer appears as the central object. The central object may be identified by being the largest object in a display.

2. Aiding a disabled viewer (e.g., an autistic person) to view modified (i.e., with removed emotions) audio/video media using audible or visual cues. System 2 may add the audible or visual cues to the modified audio/video media thereby guiding a disabled person to help them notice moments of emotion and maintain focus. The emotional cues identified by the system 2 are used to generate audible/visual cues for disabled users. For example, if a person in video data is identified as having a happy smiling face and/or speaking in a happy tone (i.e., after the emotions are removed), system 2 may generate a visual or audio cue (e.g., a red circle surrounding the person or a specified audible sound) at the moment of the emotional event. System 2 may be implemented in real-life settings through visual display, edited media (movies, television, radio, etc), in virtual simulations, etc.

System 2 of FIG. 1 comprises a computing apparatus 9, an original audio file/stream 5a, an original video file/stream 5b, and a simulated/enhanced audio and/or video file/stream 8a connected to a computing system 10 through a network 7. Network 7 may comprise any type of network including, inter alia, a local area network, (LAN), a wide area network (WAN), the Internet, etc. Original audio file/stream 5a, original video file/stream 5b, and simulated/enhanced audio and/or video file/stream 8a may each be comprised by a computer, a database, a repository, etc. Computing apparatus 9 is used as an administrator for generating simulated/enhanced audio and/or video file/stream 8a. Computing apparatus 9 may comprise, inter alia, a personal computer, a laptop computer, a computer terminal, a telephone, etc. Computing apparatus 9 may comprise a single computing apparatus or a plurality of computing apparatuses. Computing system 10 may comprise any type of computing system(s) including, inter alia, a personal computer (PC), a server computer, a database computer, etc. Computing system 10 may comprise a single computing system or a plurality of computing systems. Computing system 10 comprises a memory system 14. Memory system 14 may comprise a single memory system. Alternatively, memory system 14 may comprise a plurality of memory systems. Memory system 14 may be internal to computing system (e.g., as illustrated in FIG. 1) or external to computing system 10. Memory system 14 comprises a simulation/enhancement software application 18 and repository 17. Repository 17 may be located internal to memory system 14 or external to memory system 14. Repository 17 may be a database. Repository 17 comprises audio/video data generated and/or synchronized by simulation/enhancement software application 18 (e.g., simulated/enhanced audio and/or video file/stream 8a).

Simulation/enhancement software application 18 may comprise a plurality of software modules (as described with respect to FIG. 3, infra) for simulating disabilities and/or enhancing audio/video data streams.

Simulation/enhancement software application 18 allows for the following steps to be performed:

1. Computing system 10 receives information (i.e., original audio file/stream 5a, original video file/stream 5b, and biometrics data).
2. Simulation/enhancement software application 18 transforms the information (i.e., original audio file/stream 5a, original video file/stream 5b, and biometrics data) to generate a simulation describing how a person with a disability (e.g., autism) perceives their surroundings.
3. The simulation is presented to a viewer via an audio/video monitor. The viewer may comprise a person without a disability.
4. The simulation or original input (i.e., original audio file/stream 5a, original video file/stream 5b, and biometrics data) may additionally be modified in order to generate visual and audio modifications that enable a user with a disability to understand the simulation or original input. For example, information (e.g., visual or audio cues) may be added to the simulation to enable a user with a disability to follow the flow of any given event. The user with the disability will be able view or listen to the simulation with enhanced marks or labels that illustrate emotions (i.e., as described with reference to FIG. 5).

Figure 2:
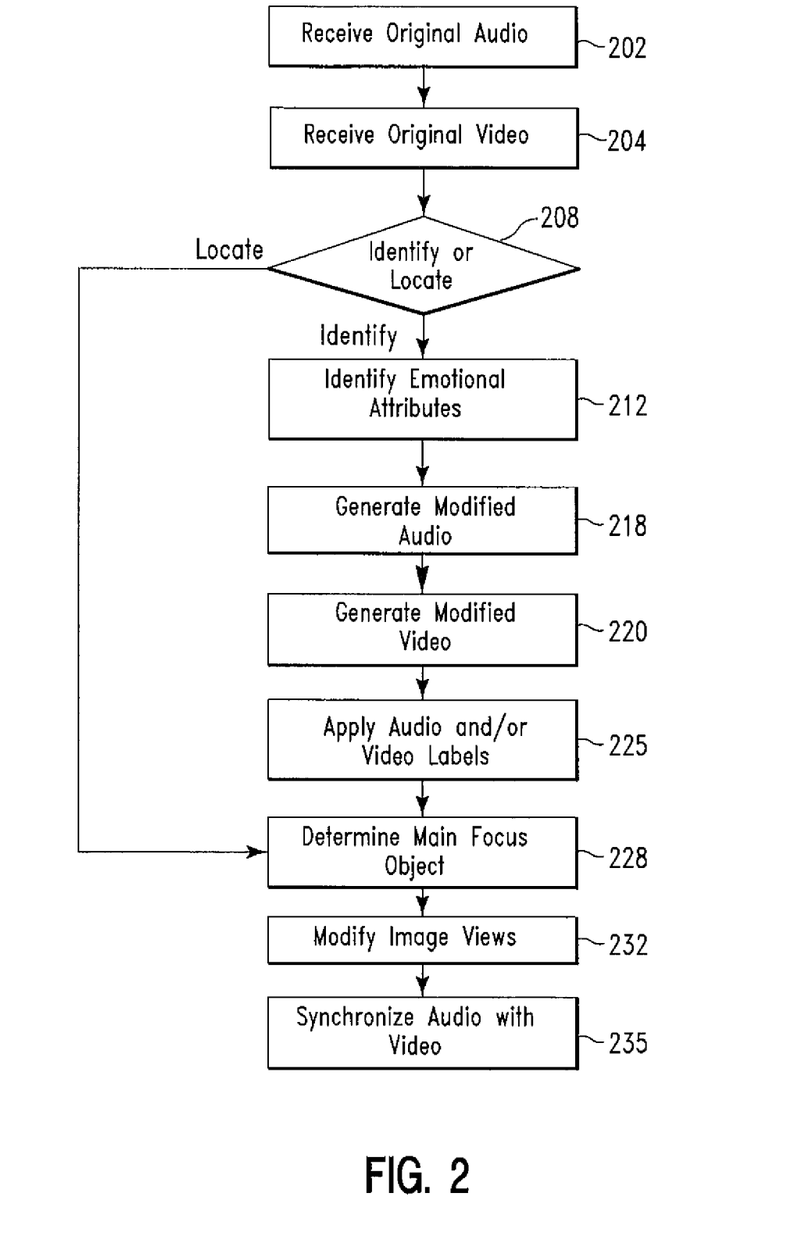
FIG. 2 illustrates an algorithm describing a process used by the system of FIG. 1 for simulating disabilities and/or enhancing audio/video data streams, in accordance with embodiments of the present invention.

FIG. 2 illustrates an algorithm describing a process used by system 2 of FIG. 1 for simulating disabilities and/or enhancing audio/video data streams, in accordance with embodiments of the present invention. In step 202, a computing system (e.g., computing system 10 in FIG. 1) receives a first (original) audio file/stream (e.g., original audio stream/file 5a in FIG. 1). The first audio file/stream includes first speech data associated with a first person. In step 204, the computing system receives a first video file/stream (e.g., original video stream/file 5b in FIG. 1). The first video file/stream includes first video data associated with the first person. The first audio file/stream and the first video file/stream may be associated with, inter alia, a television show, a movie, a live event (e.g., a concert, a live speaker, etc.), etc. In step 208, a selection is made to:

1. Identify emotional attributes associated with the first audio file/stream and/or the first video file/stream.

or

2. Locate main focus objects (i.e., locate and identify a central object in a visual image and modify the visual image such that the central object no longer appears as the central object as described with respect to FIG. 5).

If in step 208, the selection is made to locate main focus objects then in step 228, the first video file/stream (and/or first audio file/stream) is monitored and the main focus object and a background focus object are located and identified. The main focus objects may be identified by locating a largest object in an image and the background focus object may be identified by locating a smallest object in the image. In step 232, the image views (or audio levels) for the main focus object and the background focus object (e.g., a smallest object in the image, a low audio level) are modified (e.g., a size for the main focus object and a size for the background focus object may be reversed such that the main focus object appears smaller than the background focus object). In step 235, portions of the first audio file/stream are synchronized with associated portions of the first video file/stream (i.e., comprising the modified image views from step 232) and stored and/or broadcasted for a viewer.

If in step 208, the selection is made to identify emotional attributes associated with the first audio file/stream and/or the first video file/stream then in step 212, the first video file/stream and/or the first audio file/stream is monitored and emotional attributes associated with the first audio file/stream and/or the first video file/stream are identified (e.g., by detecting specific facial expressions, by detecting specific vocal expressions, etc). In step 218, a second audio file/stream associated with said first audio file/stream is generated. The second audio file/stream comprises the first speech data associated with the first person and does not comprise the emotional attributes identified in step 212. In step 220, a second video file/stream associated with said first video file/stream is generated. The second video file/stream comprises the first video data associated with the first person and does not comprise the emotional attributes identified in step 212. In (optional) step 225, visual or audio labels are added to the second audio file/stream and/or the second video file/stream (to portions associated with the emotional attributes identified in step 212). Additionally, a third audio data stream associated with the second audio data file/stream may be generated. The third audio data stream includes the second audio data file/stream and a first audible portion of the second audio data file/stream that comprises an audible label. As an additional embodiment, portions of the third audio data stream may be synchronized with associated portions of the second video data file/stream and a first audio/video data stream associated with the third audio data stream and said second video data file/stream may be generated and broadcasted. Additionally, visual objects of video data (i.e., from step 220) may be associated with an attribute of the emotional attributes of step 212. A viewable label (indicating the attribute) for a first visual object (of the visual objects) may be generated and applied to the first visual object. In response, a third video data stream associated with the second video data file/stream may be generated. The third video data stream may include the second video data file/stream and the first visual object comprising the viewable label. In (optional) step 228, the second video file/stream (e.g., comprising the visual labels or not comprising the visual labels) and/or first audio file/stream are monitored and a main focus object and a background focus object (in the second video file stream) are located and identified. The main focus objects may be identified by locating a largest object in an image and the background focus object may be identified by locating a smallest object in the image. In (optional) step 232, the image views for the main focus object and the background focus object (e.g., a smallest object in the image) are modified (e.g., a size for the main focus object and a size for the background focus object may be reversed such that the main focus object appears smaller than the background focus object). In step 235, portions of the second audio file/stream are synchronized with associated portions of the second video file/stream (e.g., comprising visual or audio labels from step 225 and/or comprising the modified image views from step 232) and stored and/or broadcasted for a viewer.

Figure 3:
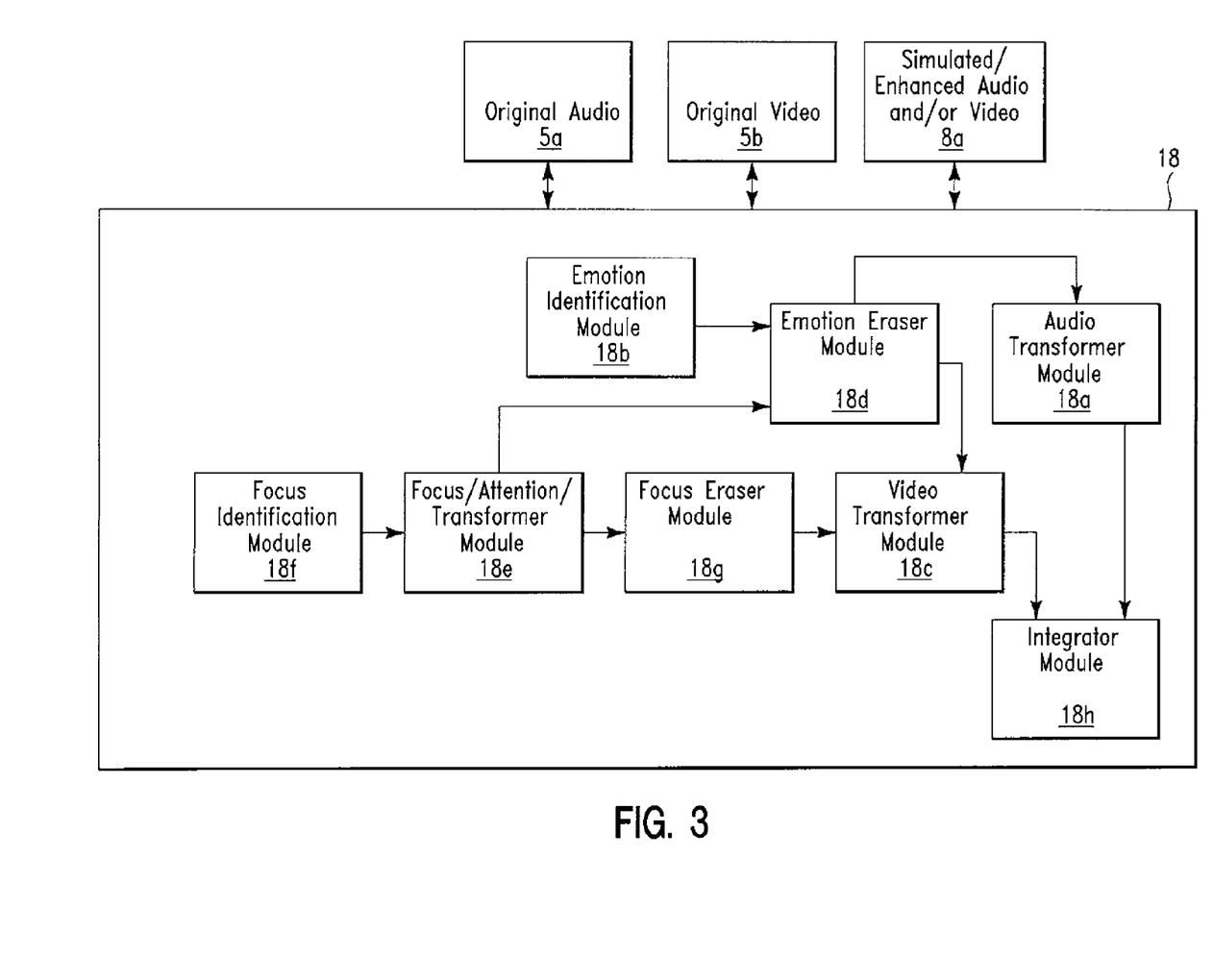
FIG. 3 illustrates a first internal block diagram view of the simulation/enhancement software application of FIG. 1, in accordance with embodiments of the present invention.

FIG. 3 illustrates a first internal block diagram view of simulation/enhancement software application 18, in accordance with embodiments of the present invention.

Simulation/enhancement software application 18 comprises a plurality of software modules:
1. Audio transformer module 18*a*.
2. Emotion identification module 18*b*.
3. Video transformer module 18*c*.
4. Emotion eraser module 18*d*.
5. Focus/attention/transformer module 18*e*.
6. Focus identification module 18*f*.
7. Focus eraser module 18*g*.
8. Integrator module 18*h*.

Audio transformer module 18*a* converts an original audio file/stream (e.g., removes emotion events, adds audio cues, etc from original audio file/stream 5*a* of FIG. 1) into simulated/enhanced/audio and/or video steams/files 8*a* (i.e., from FIG. 1). Video transformer module 18*c* converts an original video file/stream (e.g., removes emotion events, adds video cues or labels, modifies image/focus views, etc from original video file/stream 5*b* of FIG. 1) into simulated/enhanced/audio and/or video steams/files 8*a*. Emotion identification module 18*b* identifies the emotion events from original audio file/stream 5*a* and original video file/stream 5*b* using biometric recognition systems. Emotion eraser module 18*d* removes the emotion events identified by emotion identification module 18*b*. Focus identification module 18*f* identifies a main focus object and a background focus object requiring modification so that that a video object (or an audio object) that is intended to be a center of attention becomes equivalent to a background video objects (or audio objects). For example, a main character speaking in a crowd or a specific car traveling on a highway may be modified to blend into background. The main focus objects may be identified by locating a largest object in an image and the background focus object may be identified by locating a smallest object in the image. Focus/attention/transformer module 18*e* uses focus identification data generated by focus identification module 18*f* to identify and change a portion of the video object (or audio object) that presents focal elements or cues. Focus eraser module 18*g* redistributes a size of the main focus objects (i.e., identified by focus identification module 18*f*) such that all objects of visual image or audio data have equal value. Integrator module 18*h* combines transformed audio (i.e., transformed by audio transformer module 18*a*, emotion identification module 18*b*, emotion eraser module 18*d*, focus/attention/transformer module 18*e*, focus identification module 18*f*, focus eraser module 18*g*, and integrator module 18*h*) with transformed video (i.e., transformed by video transformer module 18*c*, emotion identification module 18*b*, emotion eraser module 18*d*, focus/attention/transformer module 18*e*, focus identification module 18*f*, focus eraser module 18*g*, and integrator module 18*h*).

Figure 4:
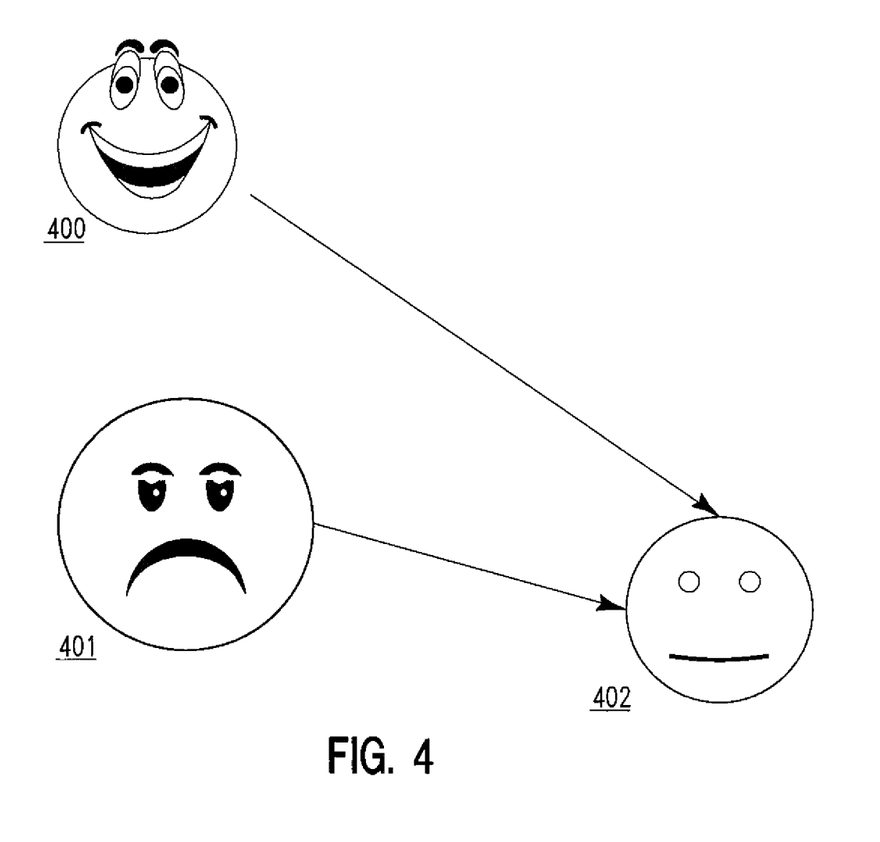
FIG. 4 is an implementation example illustrating the results of executing the emotion identification module and the emotion eraser module of FIG. 3, in accordance with embodiments of the present invention.

FIG. 4 is an implementation example illustrating the results of executing emotion identification module 18*b* and emotion eraser module 18*d* of FIG. 3, in accordance with embodiments of the present invention. Expression 400 illustrates a happy expression (i.e., a happy emotion). Expression 401 illustrates a sad expression (i.e., a sad emotion). Expression 402 illustrates a neutral expression (i.e., a neutral emotion). Expression 402 results from executing emotion eraser module 18*d* of FIG. 3 on expression 400 or 401.

Figure 5:
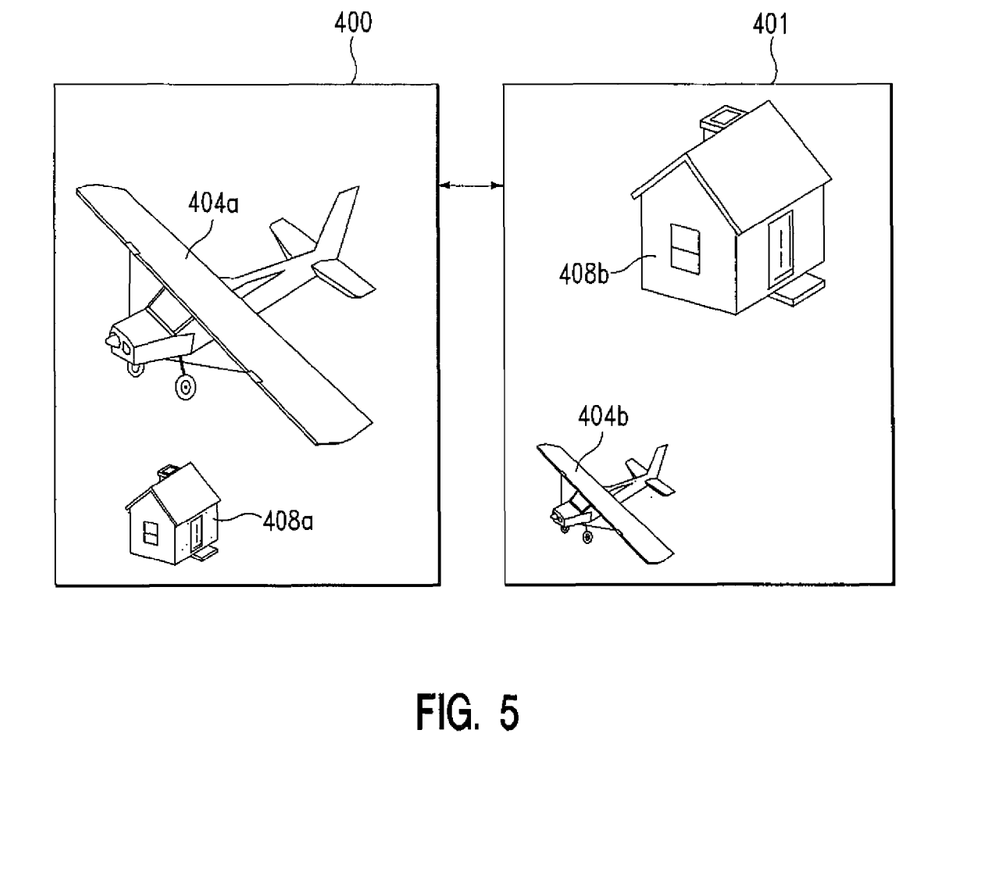
FIG. 5 is an implementation example illustrating the results of executing the focus/attention/transformer module, the focus identification module, and the focus eraser module of FIG. 3, in accordance with embodiments of the present invention.

FIG. 5 is an implementation example illustrating the results of executing focus/attention/transformer module 18*e*, focus identification module 18*f*, and focus eraser module 18*g* of FIG. 3, in accordance with embodiments of the present invention. FIG. 5 illustrates two examples for implementing focus/attention/transformer module 18*e*, focus identification module 18*f*, and focus eraser module 18*g* of FIG. 3.

EXAMPLE 1

Example 1 illustrates an embodiment associated with a disabled (e.g., autistic) viewer. In example 1, an original image 400 comprises an airplane 404*a* and a house 408*a*. House 408*a* is a video object that is a main object (i.e., intended focus). Airplane 404*a* is a video object that is a background object. Modified image 401 (i.e., modified by focus/attention/transformer module 18*e*, focus identification module 18*f*, and focus eraser module 18*g* of FIG. 3) comprises an airplane 404*b* and a house 408*b*. House 408*b* has been enlarged in sized (i.e., from house 408*a*) to illustrate the main object (i.e., intended focus). Airplane 404*b* has been reduced in size (i.e., from airplane 404*a*) to illustrate the background object.

EXAMPLE 2

Example 2 illustrates an embodiment associated with a non-disabled viewer. Example 2 simulates (i.e., for a non-disabled viewer) an environment that a disabled person (e.g., autistic) perceives. In example 2, an original image 400 comprises an airplane 404*a* and a house 408*a*. House 408*a* is a video object that is a background object. Airplane 404*a* is a video object that is a main object (i.e., intended focus). Modified image 401 (i.e., modified by focus/attention/transformer module 18*e*, focus identification module 18*f*, and focus eraser module 18*g* of FIG. 3) comprises an airplane 404*b* and a house 408*b*. House 408*b* has been enlarged in sized (i.e., from house 408*a*) to illustrate how difficult it is for a disabled viewer to identify a main object. For example, an autistic person may have difficulty identifying a central or main object in a visual image and therefore house 408*b* (background object) has been enlarged in size (i.e., from house 408*a*) to illustrate how difficult it is for a disabled viewer to identify a main object. Likewise, airplane 404*b* (i.e., main object) has been reduced in size (i.e., from airplane 404*a*).

Figure 6:
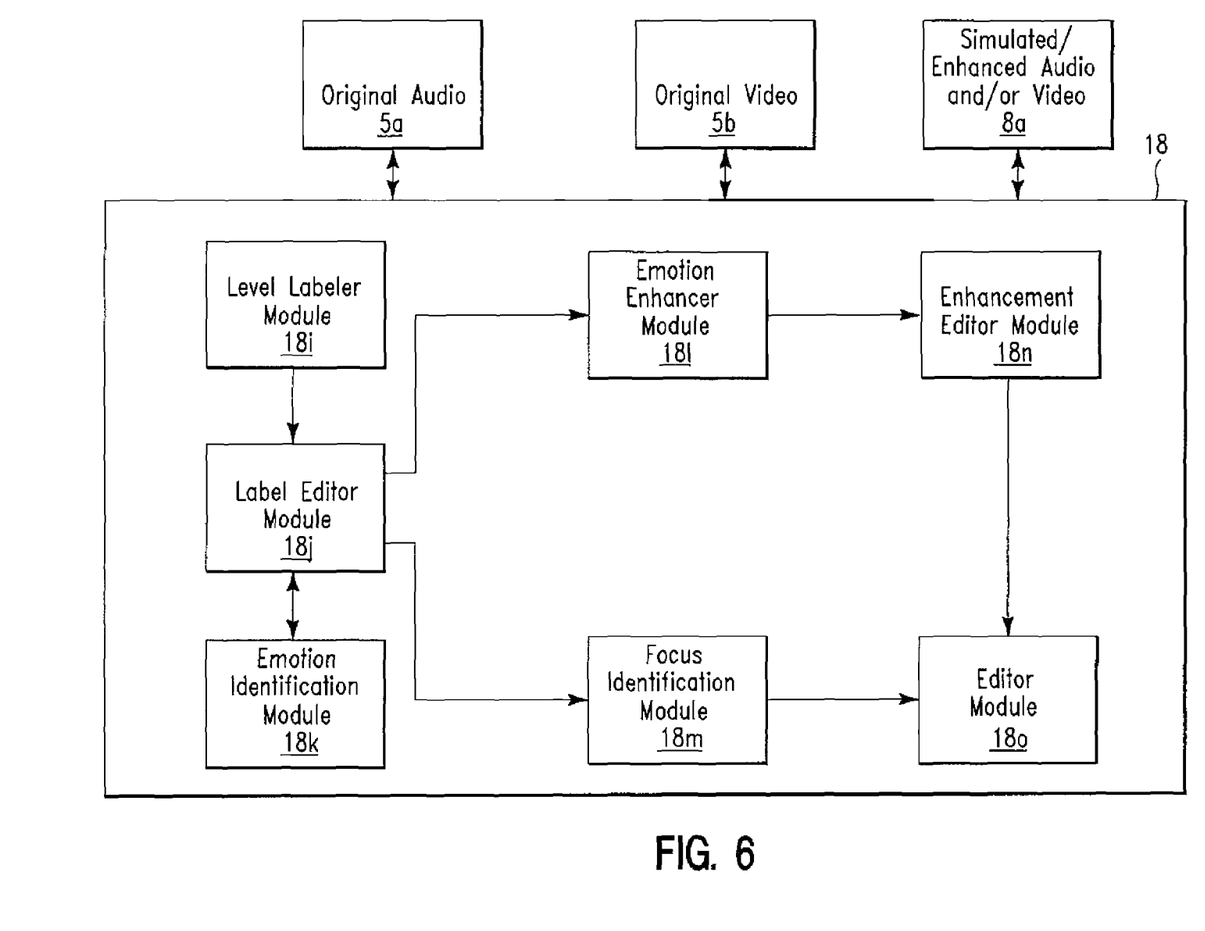
FIG. 6 illustrates a second internal block diagram view of the simulation/enhancement software application of FIG. 1, in accordance with embodiments of the present invention.

FIG. 6 illustrates a second internal block diagram view of simulation/enhancement software application 18, in accordance with embodiments of the present invention.

Simulation/enhancement software application 18 comprises a plurality of software modules:
1. Level labeler module 18*i*.
2. Label editor module 18*j*.
3. Emotion identification module 18*k*.
4. Emotion enhancer module 18*l*.
5. Focus identification module 18*m*.
6. Enhancement editor module 18*n*.
7. Editor module 18*o*.

Audio and video objects for modification are identified and labeled by level labeler module 18*i*. Labeling may comprise identifying categories of the audio and video objects. For example, identifying a face, a car, a musical instrument, etc. Label editor module 18*j* is used to edit the labels generated by level labeler module 18*i*. Emotion identification module 18*k* performs a higher level labeling process. A higher level labeling process may include identifying emotion, and focal elements in the audio and video objects. Label editor module 18*j* may be used to edit the labels generated by emotion identification module 18*k*. Focus identification module 18*m* identifies areas of focus in audio and video objects. Editor module 18*o* edits the areas of focus identified by focus identification module 18*m*. Emotion enhancer module 18*l* identifies a given emotional event with a visual cue on a display. For example, if a person on the display illustrates a happy emotion, their face may be encircled with a red perimeter. Enhancement editor may be used to edit the emotional event identified by Emotion enhancer module 18*l*.

Figure 7:
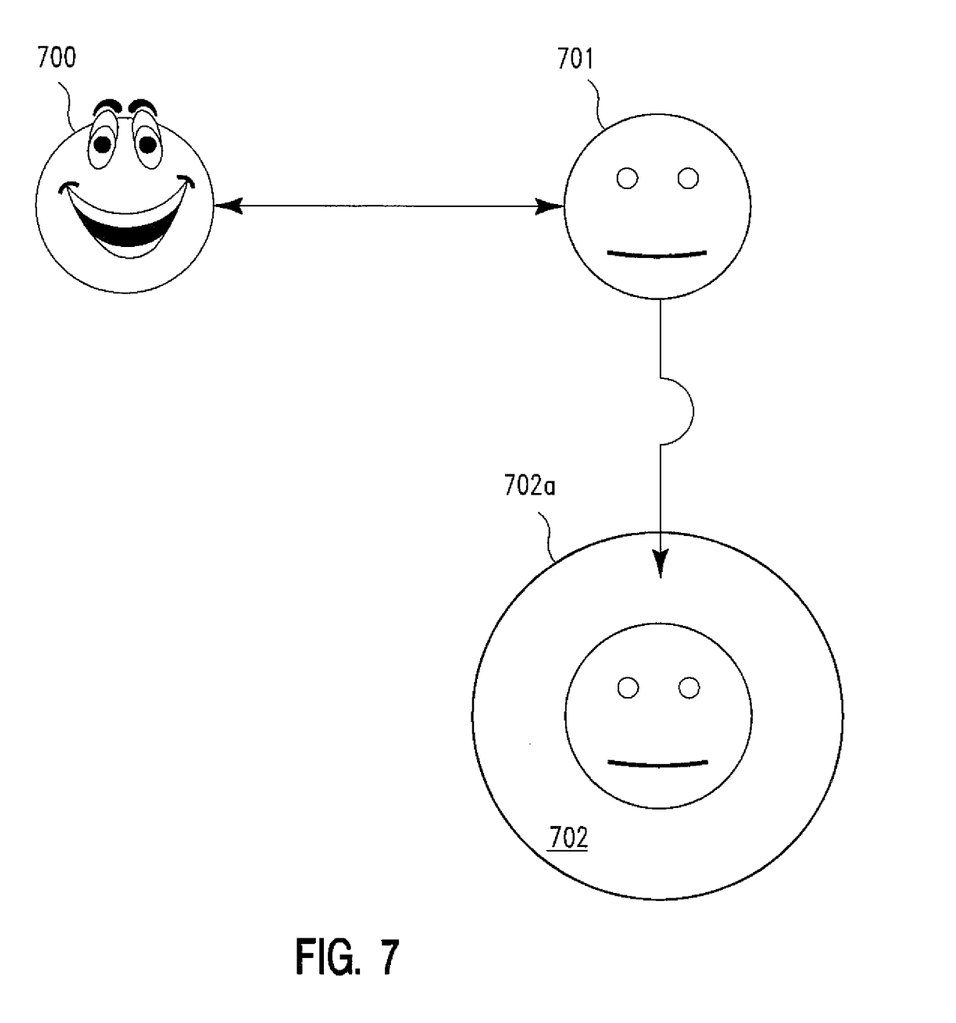
FIG. 7 is an implementation example illustrating the results of executing the emotion enhancer module of FIG. 6, in accordance with embodiments of the present invention.

FIG. 7 is an implementation example illustrating the results of executing emotion enhancer module 18*l* of FIG. 6, in accordance with embodiments of the present invention. Expression 700 illustrates a happy expression (i.e., a happy emotion). Expression 701 illustrates a neutral expression (i.e., a neutral emotion) converted from expression 700. Expression 702 illustrates expression 701 comprising an identifier 702*a* (i.e., a polygon perimeter) to help a disabled viewer recognize the happy expression removed from expression 700.

Figure 8:
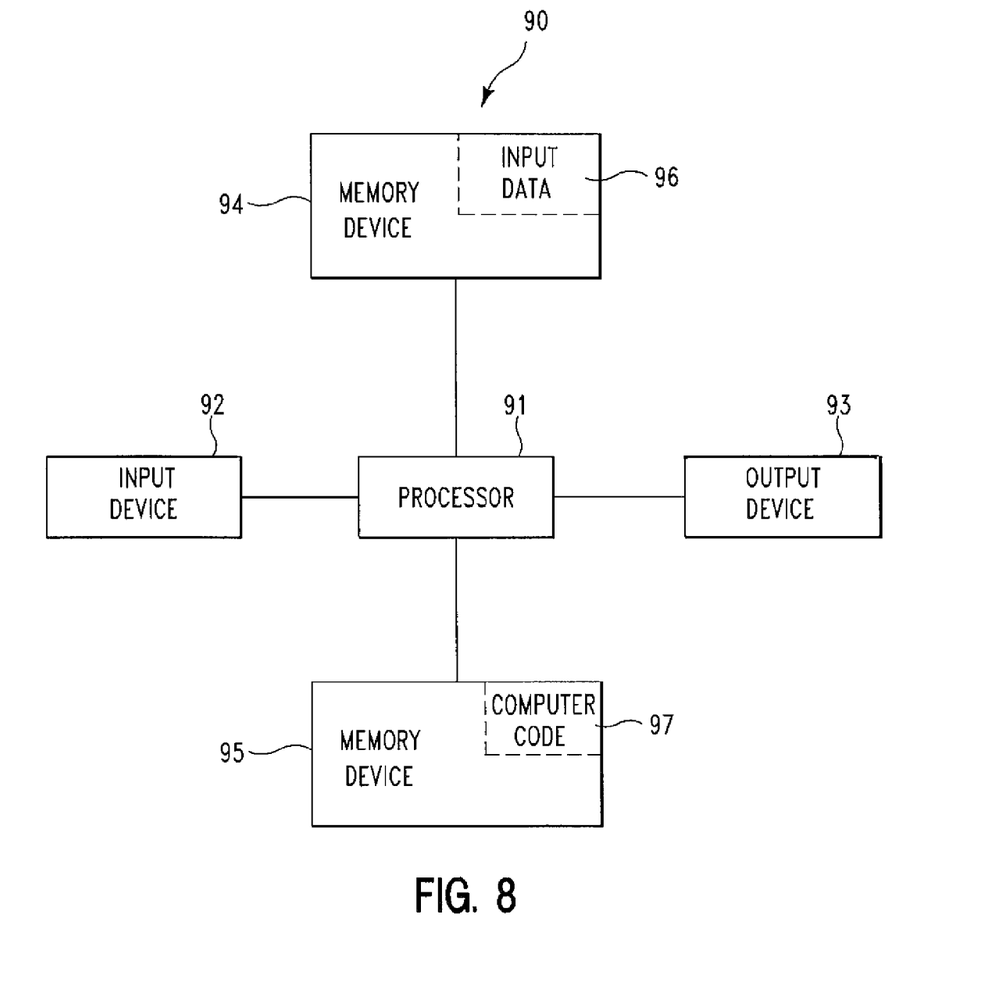
FIG. 8 illustrates a computer system used for simulating disabilities and/or enhancing audio/video data streams, in accordance with embodiments of the present invention.

FIG. 8 illustrates a computer system 90 used for simulating disabilities and/or enhancing audio/video data streams, in accordance with embodiments of the present invention. The computer system 90 comprises a processor 91, an input device 92 coupled to the processor 91, an output device 93 coupled to the processor 91, and memory devices 94 and 95 each coupled to the processor 91. The input device 92 may be, inter alia, a keyboard, a mouse, etc. The output device 93 may be, inter alia, a printer, a plotter, a computer screen (e.g., monitor 110), a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes an algorithm for simulating disabilities and/or enhancing audio/video data streams (e.g., the algorithm of FIG. 2). The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices not shown in FIG. 8) may comprise the algorithm of FIG. 2 and may be used as a computer usable medium (or a computer readable medium or a program storage device) having a computer readable program code embodied therein and/or having other data stored therein, wherein the computer readable program code comprises the computer code 97. Generally, a computer program product (or, alternatively, an article of manufacture) of the computer system 90 may comprise said computer usable medium (or said program storage device).

Still yet, any of the components of the present invention could be deployed, managed, serviced, etc. by a service provider who offers to simulate disabilities and/or enhance audio/video data streams. Thus the present invention discloses a process for deploying or integrating computing infrastructure, comprising integrating computer-readable code into the computer system 90, wherein the code in combination with the computer system 90 is capable of performing a method for simulating disabilities and/or enhancing audio/video data streams. In another embodiment, the invention provides a business method that performs the process steps of the invention on a subscription, advertising, and/or fee basis. That is, a service provider, such as a Solution Integrator, could offer to simulate disabilities and/or enhance audio/video data streams. In this case, the service provider can create, maintain, support, etc., a computer infrastructure that performs the process steps of the invention for one or more customers. In return, the service provider can receive payment from the customer(s) under a subscription and/or fee agreement and/or the service provider can receive payment from the sale of advertising content to one or more third parties.

While FIG. 8 shows the computer system 90 as a particular configuration of hardware and software, any configuration of hardware and software, as would be known to a person of ordinary skill in the art, may be utilized for the purposes stated supra in conjunction with the particular computer system 90 of FIG. 8. For example, the memory devices 94 and 95 may be portions of a single memory device rather than separate memory devices.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A simulation method, comprising:
   receiving, by a computing system, a first audio/video data stream, wherein said first audio/video data stream comprises first speech data associated with a first person;
   identifying, by said computing system, first emotional attributes comprised by said first audio/video data stream;
   generating, by said computing system in response to said identifying said first emotional attributes, an audio data stream associated with said first audio/video data stream, wherein said audio data stream comprises said first speech data, and wherein said audio data stream does not comprise said first emotional attributes;
   associating, by said computing system, a first audible portion of said audio data stream with a first attribute of said first emotional attributes;
   generating, by said computing system, an audible label for said first audible portion of said audio data stream, wherein said audible label indicates said first attribute;
   applying, by said computing system, said audible label to said first audible portion of said audio data stream;
   generating, by said computing system in response to said applying, a second audio data stream associated with said audio data stream, wherein said second audio data stream comprises said audio data stream and said first audible portion of said audio data stream comprising said audible label;
   generating, by said computing system, a video data stream associated with said audio/video data stream, wherein said video data stream comprises video data associated with said first person, and wherein said video data does not comprise said first emotional attributes;
   associating, by said computing system, a first visual object of said video data with said first attribute of said first emotional attributes;
   generating, by said computing system, a viewable label for said first visual object, wherein said viewable label indicates said first attribute of said first emotional attributes;
   applying, by said computing system, said viewable label to said first visual object; and
   generating, by said computing system in response to said applying, a second audio/video data stream associated with said second video data stream and said second audio data stream, wherein said second audio/video data stream comprises said audio data stream, said first audible portion of said audio data stream comprising said audible label, said second video data, and said first visual object comprising said viewable label.

2. The method of claim 1, further comprising:
   broadcasting, by said computing system, said second audio/video data stream.

3. The method of claim 1, wherein said first emotional attributes comprise audible and visual vocal expressions of said first person.

4. The method of claim 1, wherein said viewable label comprises a label selected from the group consisting of a polygon label comprising a perimeter for surrounding said first visual object and a label comprising different color applied to said first visual object.

5. The method of claim 1, wherein said first emotional attributes comprise facial expressions of said first person.

6. The method of claim 1, further comprising:
   providing at least one support service for at least one of creating, integrating, hosting, maintaining, and deploying computer-readable program code in the computing system, said program code being executed by the computer processor to implement said receiving, said identifying, said generating said audio data stream, said associating said first audible portion, said generating said audible label, said applying said audible label to said first audible portion of said audio data stream, said generating, said second audio data stream, said generating said video data stream, said associating said first visual object, said generating said viewable label, said applying said viewable label to said first visual object, and said generating said second audio/video data stream.

7. A computer program product, comprising a computer storage device storing a computer readable program code, said computer readable program code configured to perform a method upon being executed by a processor of a computing system, said method comprising:
   receiving, by said computing system, a first audio/video data stream, wherein said first audio/video data stream comprises first speech data associated with a first person;
   identifying, by said computing system, first emotional attributes comprised by said first audio/video data stream;
   generating, by said computing system in response to said identifying said first emotional attributes, an audio data stream associated with said first audio/video data stream, wherein said audio data stream comprises said first speech data, and wherein said audio data stream does not comprise said first emotional attributes;
   associating, by said computing system, a first audible portion of said audio data stream with a first attribute of said first emotional attributes;

generating, by said computing system, an audible label for said first audible portion of said audio data stream, wherein said audible label indicates said first attribute;

applying, by said computing system, said audible label to said first audible portion of said audio data stream;

generating, by said computing system in response to said applying, a second audio data stream associated with said audio data stream, wherein said second audio data stream comprises said audio data stream and said first audible portion of said audio data stream comprising said audible label;

generating, by said computing system, a video data stream associated with said audio/video data stream, wherein said video data stream comprises video data associated with said first person, and wherein said video data does not comprise said first emotional attributes;

associating, by said computing system, a first visual object of said video data with said first attribute of said first emotional attributes;

generating, by said computing system, a viewable label for said first visual object, wherein said viewable label indicates said first attribute of said first emotional attributes;

applying, by said computing system, said viewable label to said first visual object; and generating, by said computing system in response to said applying, a second audio/video data stream associated with said second video data stream and said second audio data stream, wherein said second audio/video data stream comprises said audio data stream, said first audible portion of said audio data stream comprising said audible label, said second video data, and said first visual object comprising said viewable label.

8. The computer program product of claim 7, wherein said method further comprises:

broadcasting, by said computing system, said second audio/video data stream.

9. The computer program product of claim 7, wherein said first emotional attributes comprise audible and visual vocal expressions of said first person.

10. The computer program product of claim 7, wherein said viewable label comprises a label selected from the group consisting of a polygon label comprising a perimeter for surrounding said first visual object and a label comprising different color applied to said first visual object.

11. The computer program product of claim 7, wherein said first emotional attributes comprise facial expressions of said first person.

12. A computing system comprising a processor coupled to a computer-readable memory unit, said memory unit comprising a computer readable code configured to be executed by the processor to perform a method comprising:

receiving, by said computing system, a first audio/video data stream, wherein said first audio/video data stream comprises first speech data associated with a first person;

identifying, by said computing system, first emotional attributes comprised by said first audio/video data stream;

generating, by said computing system in response to said identifying said first emotional attributes, an audio data stream associated with said first audio/video data stream, wherein said audio data stream comprises said first speech data, and wherein said audio data stream does not comprise said first emotional attributes;

associating, by said computing system, a first audible portion of said audio data stream with a first attribute of said first emotional attributes;

generating, by said computing system, an audible label for said first audible portion of said audio data stream, wherein said audible label indicates said first attribute;

applying, by said computing system, said audible label to said first audible portion of said audio data stream;

generating, by said computing system in response to said applying, a second audio data stream associated with said audio data stream, wherein said second audio data stream comprises said audio data stream and said first audible portion of said audio data stream comprising said audible label;

generating, by said computing system, a video data stream associated with said audio/video data stream, wherein said video data stream comprises video data associated with said first person, and wherein said video data does not comprise said first emotional attributes;

associating, by said computing system, a first visual object of said video data with said first attribute of said first emotional attributes;

generating, by said computing system, a viewable label for said first visual object, wherein said viewable label indicates said first attribute of said first emotional attributes;

applying, by said computing system, said viewable label to said first visual object; and generating, by said computing system in response to said applying, a second audio/video data stream associated with said second video data stream and said second audio data stream, wherein said second audio/video data stream comprises said audio data stream, said first audible portion of said audio data stream comprising said audible label, said second video data, and said first visual object comprising said viewable label.

13. The computing system of claim 12, wherein said method further comprises:

broadcasting, by said computing system, said second audio/video data stream.

14. The computing system of claim 12, wherein said first emotional attributes comprise audible and visual vocal expressions of said first person.

15. The computing system of claim 12, wherein said viewable label comprises a label selected from the group consisting of a polygon label comprising a perimeter for surrounding said first visual object and a label comprising different color applied to said first visual object.

16. The computing system of claim 12, wherein said first emotional attributes comprise facial expressions of said first person.

* * * * *